US006911209B1

(12) United States Patent
Lehtonen et al.

(10) Patent No.: US 6,911,209 B1
(45) Date of Patent: Jun. 28, 2005

(54) METHOD OF TREATING SICK SINUS SYNDROME WITH LEVOSIMENDAN

(75) Inventors: Lasse Lehtonen, Espoo (FI); Mikhail Ruda, Moscow (RU); Jeffrey Hosenpud, Milwaukee, WI (US)

(73) Assignee: Orion Corporation, Espoo (FI)

( * ) Notice: Subject to any disclaimer, the term of this patent is extended or adjusted under 35 U.S.C. 154(b) by 438 days.

(21) Appl. No.: 10/111,099

(22) PCT Filed: Oct. 20, 2000

(86) PCT No.: PCT/FI00/00915

§ 371 (c)(1),
(2), (4) Date: Aug. 23, 2002

(87) PCT Pub. No.: WO01/28560

PCT Pub. Date: Apr. 26, 2001

(30) Foreign Application Priority Data

Oct. 22, 1999 (FI) .............................. 19992298

(51) Int. Cl.$^7$ ............................. A61K 9/20; A61K 9/70
(52) U.S. Cl. ...................... 424/400; 424/449; 424/464; 514/772.6
(58) Field of Search ............................... 424/400, 449, 424/469

(56) References Cited

U.S. PATENT DOCUMENTS 5,424,428 A    6/1995  Nore et al. .................. 544/239

FOREIGN PATENT DOCUMENTS

| WO | WO93/21921 | 11/1993 |
| WO | WO 98/18475 | 5/1998 |

OTHER PUBLICATIONS

Janssen et al., "Levosimendan improves diastolic and systolic function in failing human myocardium," European Journal of Pharmacology, vol. 404, pp. 191–199 (2000).
Toivonen et al., "Electrophysiologic Effects of a Calcium Sensitizer Inotrope Levosimendan Administered Intravenously in Patients with Normal Cardiac Function," Journal of Cardiovascular Pharmacology, vol. 35, pp. 664–669 (2000).

Alagona, 'Advances in pacing for the patient with sick sinus syndrome', Current Opinion in Cardiology, vol. 12, pp. 3–11, 1997.
Sundberg et al., 'Hemodynamic and Neurohumoral Effects of Levosimendan, a New Calcium Sensitizer, at Rest and During Exercise in Healthy Men', Am J Cardiol, vol. 75, pp. 1061–1066, 1995.
Lilleberg et al., 'Dose–Range Study of a New Calcium Sensitizer, Levosimendan, in Patients with Left Ventricular Dysfunction', Journal of Cardiovascular Pharmacology, vol. 26 (suppl. 1), pp. S63–S69, 1985.
Sandell et al., 'Pharmacokinetics of Levosimendan in Healthy Volunteers and Patients with Congestive Heart Failure', Journal of Cardiovascular Pharmacolohy, vol. 26, pp. 57–62, 1995.
Lilleberg et al., 'Effects of a new calcium sensitizer, levosimendan, on haemodynamics, coronary blood flow and myocardial substrate utilization early after coronary artery bypass grafting', European Heart Journal, vol. 19, pp. 660–668, 1998.
Harjola et al., 'Oral Levosimendan Improves Cardiac Function and Hemodynamics in Patients with Severe Congestive Heart Failure', Am J Cardiol, vol. 83, pp. 4 (l)–8 (l), 1999.
Singh et al., 'Effects of Levosimendan on Cardiac arrhythimia : Electrophysiologic and Ambulatory Electrocardiographic Findings in Phase II and Phase III Clinical Studies in Cardiac Failure', Am J Cardiol, vol. 83, pp. 16 (l)–20 (l), 1999.
Du Toit et al., 'Levosimendan: Effects of a Calcium Sensitizer on Function and Arrhythmias and Cyclic Nucleotide Levels during Ischemia/Reperfusion in the LangendorffPerfused Guinea Pig Heart', The Journal of Pharmacology and Experimental Therapeutics, vol. 290, pp. 505–514, 1999.

*Primary Examiner*—Thurman K. Page
*Assistant Examiner*—Sharon Howard
(74) *Attorney, Agent, or Firm*—Finnegan, Henderson, Farabow, Garrett & Dunner, LLP

(57) ABSTRACT

Levosimendan, or (−)-[[4-(1,4,5,6-tetrahydro-4-methyl-6-oxo-3-pyridazinyl)phenyl]hydrazono]propanedinitrile, which has been previously suggested for the treatment of congestive heart failure is useful in the treatment of sick sinus syndrome and/or sinoatrial conduction disorders.

8 Claims, No Drawings

METHOD OF TREATING SICK SINUS SYNDROME WITH LEVOSIMENDAN

This application is a national stage filing of PCT International Application No. PCT/FI00/00915, filed on Oct. 20, 2000. This application also claims the benefit of priority to Finnish patent application no. 19992298, filed on Oct. 22, 1999.

TECHNICAL FIELD

The present invention relates to a method for the treatment of sick sinus syndrome and/or sinoatrial conduction disorders by administering levosimendan, or (−)-[[4-(1,4,5, 6-tetrahydro-4-methyl-6-oxo-3-pyridazinyl)phenyl] hydrazono]propanedinitrile (I), or pharmaceutically acceptable salts thereof, to a patient in need of such treatment.

BACKGROUND OF THE INVENTION

Levosimendan, which is the (−)-enantiomer of [[4-(1,4, 5,6-tetrahydro-4-methyl-6-oxo-3-pyridazinyl)phenyl] hydrazono]propanedinitrile, and the method for its preparation is described in EP 565546 B1. Levosimendan is potent in the treatment of heart failure and has significant calcium dependent binding to troponin. Levosimendan is represented by the formula:

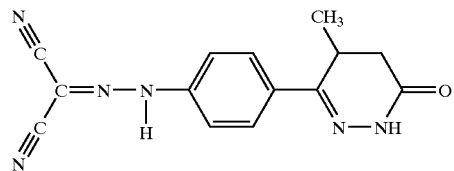

I

The hemodynamic effects of levosimendan in man are described in Sundberg, S. et al., Am. J. Cardiol., 1995; 75: 1061–1066 and in Lilleberg, J. et al., J. Cardiovasc. Pharmacol., 26(Suppl.1), S63–S69, 1995. Pharmacokinetics of levosimendan in man after i.v. and oral dosing is described in Sandell, E.-P. et al., J. Cardiovasc. Pharmacol., 26(Suppl.1), S57–S62, 1995. The use of levosimendan in the treatment of myocardial ischemia is described in WO 93/21921. Clinical studies have confirmed the beneficial effects of levosimendan in heart failure patients.

The electrical signal that initiates each normal heart beat arises from a small structure located at the top of right atrium. The structure is called "sinus node" or "sinoatrial node". The sinus node is the natural pacemaker of the heart. It initiates the cardiac cycle of systole and diastole phases by generating an electrical impulse that spreads over the right and left atria, causing them to contract almost simultaneously. This electrical impulse is generated by the depolarization of the myocardial cells of the sinus node. The atria are electrically insulated from the ventricles by the atrioventricular (AV) groove. There is one area of the heart where the atria and the ventricles are electrically connected. This connection which actually comprises the second electrical structure of the heart is called the atrioventricular node or AV node. All electrical signals from the atrium must pass through the AV node in order to get to the ventricles. The impulse then continues from the AV node through the bundle of special cells designed to rapidly conduct the electrical signal through the ventricles. These fibers eventually branch out to the distant ventricular tissues. Stimulation of these fibers causes the ventricles to contract almost simultaneously and discharge of blood into the circulatory systems.

Various dysfunctions of the heart lead to altered beating. One such dysfunction is sick sinus syndrome (SSS), a progressive sinus node dysfunction often with further involvement of sinoatrial conduction disorders. Its diagnostic criteria include (i) inappropriate sinus rate-bradycardia for the underlying physiologic state (chronotropic incompetence), (ii) significant sinus pauses (<3 seconds) or arrest, (iii) sinoatrial exit block not related to drug therapy, (iv) chronic atrial fibrillation with an unacceptably slow ventricular response, (v) tachycardia-bradycardia syndrome, (vi) prolonged corrected sinus node recovery time and (vii) prolonged sinus node refractoriness and sinoatrial conduction time (Alagona, MD, Current Opinion in Cardiology, 1997, 12:3–11).

SSS with severe slowing of the heart beat (bradycardia) is associated with significant symptoms such as fatigue and shortness of breath. Sometimes the sinus node stops firing temporarily, and long pauses in the heart rhythm may result. The causes of sick sinus syndrome are usually intrinsic such as aging, sinoatrial nodal artery disease, scarring, or physical damages. There can also be extrinsic sinus node problems due to medications, hormonal conditions (such as an underactive thyroid gland) or neurological imbalances.

At the moment, there is no successful medical treatment for sick sinus syndrome. It is usually treated with a permanent pacemaker, a small electronic device implanted in the body of the patient. Thus, there is a strong need for a drug that would be effective in the treatment of sick sinus syndrome.

SUMMARY OF THE INVENTION

It has now been found that levosimendan has unexpected benefits in the treatment of sick sinus syndrome and/or sinoatrial conduction disorders.

Therefore, the present invention provides the use of (−)-[[4-(1,4,5,6-tetrahydro-4-methyl-6-oxo-3-pyridazinyl) phenyl]hydrazono]propanedinitrile or a pharmaceutically acceptable salt thereof in the manufacture of a medicament for the treatment of sick sinus syndrome and/or sinoatrial conduction disorders.

The present invention also provides a method for the treatment of sick sinus syndrome and/or sinoatrial conduction disorders in a patient, said method comprising administering to a patient in need thereof an effective amount of (−)-[[4-(1,4,5,6-tetrahydro-4-methyl-6-oxo-3-pyridazinyl) phenyl]hydrazono]propanedinitrile or a pharmaceutically acceptable salt thereof.

DETAILED DESCRIPTION

The method of the invention comprises a step of administering to a subject an amount of levosimendan effective to restore the function of sinus node and/or to improve sinoatrial conduction of the heart. The administration can be effected enterally, e.g. orally or rectally, or parenterally, e.g. intravenously or transdermally.

The effective amount of levosimendan to be administered to a subject depends upon the condition to be treated, the route of administration, age, weight and the condition of the patient. In general levosimendan is administered orally to man in daily dose from about 0.1 to 20 mg, preferably from 0.2 to 15 mg, more preferably from 0.5 to 10 mg, given once a day or divided into several doses a day, depending on the age, body weight and condition of the patient. Levosimendan can be administered by intravenous infusion using the infusion rate typically from about 0.01 to 10 μg/kg/min, more typically from about 0.02 to 5 μg/kg/min. For example, using an infusion of 24 hours a rate of 0.05–0.2 μg/kg/min is considered suitable.

Levosimendan is formulated into dosage forms suitable for the treatment of sick sinus syndrome and sinoatrial conduction disorders using the principles known in the art. It is given to a patient as such or preferably in combination with suitable pharmaceutical excipients in the form of tablets, dragees, capsules, suppositories, emulsions, suspensions or solutions whereby the contents of the active compound in the formulation is from about 0.5 to 100% per weight. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds, release controlling components and other ingredients normally used in this field of technology may be also used.

For oral administration in tablet form, suitable carriers and excipients include e.g. lactose, corn starch, magnesium stearate, calcium phosphate and talc. For oral administration in capsule form, useful carriers and excipients include e.g. lactose, corn starch, magnesium stearate and talc. For controlled release oral compositions release controlling components can be used. Typical release controlling components include hydrophilic gel forming polymers such as hydroxypropylmethyl cellulose, hydroxypropyl cellulose, carboxymethyl celluloses, alginic acid or a mixture thereof; vegetable fats and oils including vegetable solid oils such as hydrogenated soybean oil, hardened castor oil or castor seed oil (sold under trade name Cutina HR), cotton seed oil (sold under the trade names Sterotex or Lubritab) or a mixture thereof, fatty acid esters such as triglycerides of saturated fatty acids or their mixtures e.g. glyceryl tristearates, glyceryl tripalmitates, glyceryl trimyristates, glyceryl tribehenates (sold under the trade name Compritol) and glyceryl palmitostearic acid ester.

Tablets can be prepared by mixing the active ingredient with the carriers and excipients and compressing the powdery mixture into tablets. Capsules can be prepared by mixing the active ingredient with the carriers and excipients and placing the powdery mixture in capsules, e.g. hard gelatin capsules. Typically a tablet or a capsule comprises from about 0.1 to 10 mg, more typically 0.2 to 5 mg, of levosimendan.

Formulations suitable for intravenous administration such as injection or infusion formulation, comprise sterile isotonic solutions of levosimendan and vehicle, preferably aqueous solutions. Typically an intravenous infusion solution comprises from about 0.01 to 0.1 mg/ml of levosimendan.

Salts of levosimendan may be prepared by known methods. Pharmaceutically acceptable salts are useful as active medicaments, however, preferred salts are the salts with alkali or alkaline earth metals.

EXAMPLES

Pharmaceutical Example

| Hard gelatin capsule size 3 | |
|---|---|
| Levosimendan | 2.0 mg |
| Lactose | 198 mg |

The pharmaceutical preparation in the form of a capsule was prepared by mixing levosimendan with lactose and placing the powdery mixture in hard gelatin capsule.

Clinical Data

The underlying heart rhythm of a 77 year-old patient on intravenous milrinone was wandering atrial pacemaker with a first degree AV block alternating with a junctional rhythm and sinus rhythm. The overall heart rate was around 70 bpm. Because of failure to wean the milrinone the patient was entered into oral levosimendan first at 1 mg followed by 2 mg and subsequently by 4 mg qd. His heart rate steadily increased to over 90 bpm. His levosimendan dose was reduced to 2 mg and maintained at that dose during the taper of intravenous milrinone. His cardiac rhythm did regularize with a vast majority of the beats being sinus node in origin and he maintained an overall heart rate in the 80–85 bpm range. Milrinone was tapered off and the patient could be transferred out of the intensive care unit. The patient's dose of levosimendan was continued at 1 mg three times a day.

What is claimed is:

1. A method for the treatment of sick sinus syndrome and/or a sinoatrial conduction disorder in a patient, which comprises administering to the patient in need thereof an effective amount of (−)-[[4-(1,4,5,6-tetrahydro-4-methyl-6-oxo-3-pyridazinyl)phenyl]hydrazono]propanedinitrile or a pharmaceutically acceptable salt thereof.

2. A method as claimed in claim 1, which comprises enterally administering the effective amount of (−)-[[4-(1,4,5,6-tetrahydro-4-methyl-6-oxo-3-pyridazinyl)phenyl]hydrazono]propanedinitrile or a pharmaceutically acceptable salt thereof to the patient.

3. A method as claimed in claim 2, wherein the administration is oral administration.

4. A method as claimed in claim 2, wherein the administration is rectal administration.

5. A method as claimed in claim 1, which comprises parenterally administering the effective amount of (−)-[[4-(1,4,5,6-tetrahydro-4-methyl-6-oxo-3-pyridazinyl)phenyl]hydrazono]propanedinitrile or a pharmaceutically acceptable salt thereof to the patient.

6. A method as claimed in claim 5, wherein the administration is intravenous administration.

7. A method as claimed in claim 5, wherein the administration is transdermal administration.

8. A method as claimed in claim 1, wherein the pharmaceutically acceptable salt is a salt with an alkali or alkaline earth metal.

* * * * *